United States Patent [19]
Walls

[11] Patent Number: 5,587,736
[45] Date of Patent: Dec. 24, 1996

[54] STERILIZABLE CCD VIDEO CAMERA

[75] Inventor: Robert R. Walls, Santa Barbara, Calif.

[73] Assignee: Envision Medical Corporation, Goleta, Calif.

[21] Appl. No.: 18,053

[22] Filed: Feb. 16, 1993

[51] Int. Cl.$^6$ .................................................... A61B 1/04
[52] U.S. Cl. ............................................. 348/65; 600/101
[58] Field of Search .................................. 348/65, 76, 82, 348/83, 262, 265, 373, 374, 164; 128/4; 361/814; 310/334; 250/352, 370.15, 261; 600/101; H04N 5/225

[56] References Cited

U.S. PATENT DOCUMENTS

| | | | |
|---|---|---|---|
| 4,524,385 | 6/1985 | Billingsley et al. | 348/164 |
| 4,694,175 | 9/1987 | Buller | 250/370.15 |
| 4,695,881 | 9/1987 | Kennedy et al. . | |
| 4,756,304 | 7/1988 | Watanabe . | |
| 4,799,474 | 1/1989 | Ueda . | |
| 4,914,521 | 4/1990 | Adair . | |
| 4,937,450 | 6/1990 | Wakabayashi et al. | 250/352 |
| 4,965,601 | 10/1990 | Canty . | |
| 4,969,035 | 11/1990 | Dawson . | |
| 4,979,498 | 12/1990 | Oneda et al. . | |
| 4,993,405 | 2/1991 | Takamura et al. . | |
| 5,012,102 | 4/1991 | Gowlett | 250/352 |
| 5,045,699 | 9/1991 | Schulze et al. . | |
| 5,063,461 | 11/1991 | Copenhaver et al. | 348/373 |
| 5,065,029 | 11/1991 | Krivanek et al. . | |
| 5,124,797 | 6/1992 | Williams et al. . | |
| 5,156,141 | 10/1992 | Krebs et al. | 128/4 |
| 5,177,364 | 1/1993 | Gowlett et al. | 250/370.15 |
| 5,187,939 | 2/1993 | Skertic et al. | 250/352 |
| 5,220,184 | 6/1993 | Philbrick et al. | 348/262 |
| 5,225,677 | 7/1993 | Yeh et al. | 250/370.15 |
| 5,228,430 | 7/1993 | Sakamoto | 348/65 |
| 5,235,184 | 8/1993 | Paulson | 250/238 |
| 5,255,081 | 10/1993 | Miyamoto et al. | 348/265 |
| 5,258,892 | 11/1993 | Stanton et al. | 361/814 |
| 5,270,544 | 12/1993 | Taira | 250/370.15 |
| 5,274,237 | 12/1993 | Gallagher et al. | 250/370.15 |
| 5,294,861 | 3/1994 | Nattermann | 310/334 |
| 5,296,710 | 3/1994 | Ohno et al. | 250/370.15 |
| 5,317,157 | 3/1994 | Yoshida et al. | 250/352 |

FOREIGN PATENT DOCUMENTS

WO9015569  12/1990  WIPO .

Primary Examiner—Tommy P. Chin
Assistant Examiner—Richard Lee
Attorney, Agent, or Firm—Lyon & Lyon

[57] ABSTRACT

An apparatus and related method for protecting a CCD from thermal damage or degradation, including a housing having double walls separated by a vacuum, and a support member for positioning the CCD within the housing. The housing may also act as a barrier to electromagnetic interference and contaminants.

5 Claims, 3 Drawing Sheets

STERILIZABLE CCD VIDEO CAMERA

BACKGROUND OF THE INVENTION

The field of the invention relates generally to the protection of a CCD video camera.

In recent years, the need for small, lightweight video cameras has rapidly developed in both the medical and industrial fields. One medical application requiring such a video camera is laparoscopy wherein an endoscope typically having a diameter of 5 to 10 mm is passed through a small incision in the patient to permit viewing of the surgical site. Earlier laparoscopic procedures required the surgeon to view the body cavity directly through the endoscope eyepiece. Now, a camera head may be attached to the endoscope eyepiece and a flexible cable typically connects the camera head to the remaining camera electronics at a remote location which are attached to a video monitor. This surgical visualization system allows the surgical team to view the interior of a body cavity on the monitor.

The surgical visualization system typically comprises components such as the endoscope, illumination light fiber bundle, coupling optics (i.e., couples the camera and endoscope) and camera head. Typically, the camera head contains an imager or charge-coupled device ("CCD") which receives the surgical site image from the coupling or other optics and transmits the image to associated electronics in preparation for video display. Because the surgical visualization components are used within a sterile field (i.e., an arbitrary area around the surgical site in which everything is sterile) in the operating room, they must be sterilized like other surgical instruments. Several sterilization procedures have been used in the past.

The steam autoclaving process wherein the instrument is inserted into a steam autoclave for approximately 45 minutes, is used for instruments that can withstand the high temperature for the necessary amount of time. Instruments which cannot withstand the autoclave process such as a camera head including a CCD are treated by less effective means which disinfect but do not sterilize, such as the cold soak process or by ethylene oxide gas exposure. A third alternative suitable for a camera head including a CCD is to apply a disposable sterile plastic cover over the camera head which remains in place during surgery. This alternative is also less effective because there is still a non-sterilized instrument within the cover which could infect the surgical site if the cover is punctured or falls off. Furthermore, the surgical instrument may become difficult to manipulate due to the cover's presence. Still further, because the cover is disposable, its cost is incurred for each surgical procedure.

Recently, short exposure steam sterilization, or flash sterilization, has been developed to sterilize instruments so that they may be immediately used. Flash sterilization may reduce the steam autoclave time of 45 minutes to less than five minutes but still involves increased temperatures. In any event, the advent of increasingly virulent contaminants which may not be eliminated by techniques which only disinfect but do not sterilize, and the need to quickly prepare instruments between surgical procedures has made flash steam sterilization the method of choice for many surgical instruments.

Flash sterilizable versions of all the surgical visualization components listed above currently exist except for the camera head including the CCD. Typically the CCD would be damaged or otherwise degraded if exposed to sterilization temperatures thereby rendering the CCD useless when later operated to view a surgical site. As a result, this generally requires that the camera head be disinfected with the less effective means set forth above or that a protective cover be used. Accordingly, there is a need for an apparatus containing a CCD which may protect the CCD from the increased temperatures present during flash sterilization.

An industrial application requiring a small video camera or CCD involves observation of high-temperature industrial processes such as those occurring in nuclear power generating stations, furnaces or engine compartments. Here, the CCD operates to observe the high-temperature process as it occurs. As in medical sterilization, the CCD would be damaged or its picture degraded if it were exposed to the increased temperatures associated with such industrial processes. Accordingly, there is a need for an apparatus containing a CCD which may protect the CCD from the increased temperatures associated with high-temperature industrial processes.

In addition to protection from heat which arises during medical or industrial applications, the CCD should be situated in the camera head or apparatus so that it is shielded from electromagnetic interference as well as from gas, water and other contaminants. Accordingly, there is a need for an apparatus which provides such protection.

SUMMARY OF THE INVENTION

In a first aspect of the invention, an apparatus having double walls separated by a vacuum, and a support member mounted within the apparatus for positioning heat sensitive components contained therein is described.

In a second aspect of the invention, an apparatus is described which includes a housing having tight seals which encloses and protects sensitive components contained therein from electromagnetic interference and contaminant materials.

DESCRIPTION OF THE PREFERRED EMBODIMENT

Figure 1:
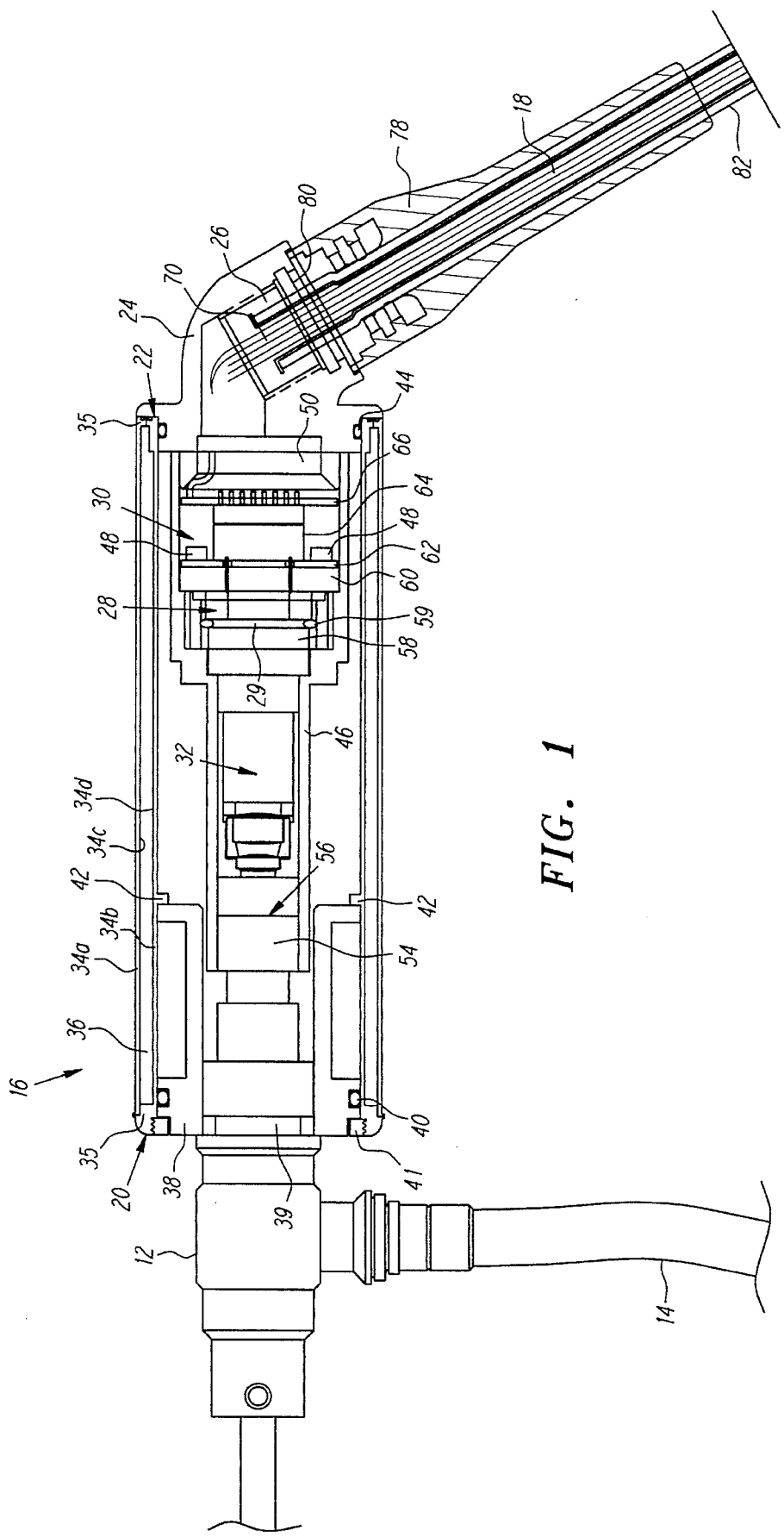
FIG. 1 is a side view of surgical visualization components including a section view of a protective housing containing one CCD.

Referring to FIG. 1, an endoscope 12, an illumination fiber bundle 14, a section view of a housing 16 and a cable 18 are generally shown. The distal portion (not shown) of endoscope 12 is inserted into the patient through an incision. Attached to the endoscope 12 is illumination fiber bundle 14 which provides light for viewing a particular body cavity. Typically, endoscope 12, and illumination fiber bundle 14 are sterilizable.

The endoscope 12 is attached to the housing forward end 20 while attached to the housing rear end 22 is a backing 24. The backing 24 includes a cable entry 26 to receive cable 18. Cable 18 is typically about ten feet long and extends from the backing 24 to associated camera electronics (not shown) which are in turn connected to a video monitor (not shown) for video display of the body cavity being viewed.

The housing 16 generally encloses a CCD 28 which includes a CCD faceplate 29, and electronics 30 operative with and coupled to the CCD 28. The electronics 30 receive the image from CCD 28 and prepare it for transmission to the associated camera electronics. The housing 16 may also enclose a portion of the endoscope 12 and the coupling optics 32 which serve to transfer the image from the endoscope 12 to the CCD 28.

Existing CCDs typically exhibit a degradation temperature above which the CCD may be damaged, or the image produced by the CCD is generally degraded. The degradation of image quality generally results from thermal damage to the color filters and adhesives of the CCD. While degradation temperatures may vary between CCDs, many existing CCDs experience degradation and/or damage when exposed to temperatures exceeding about 80 degrees Centigrade. However, sterilization procedures typically employ wet steam to bring all potentially contaminated surfaces to a temperature of approximately 134 degrees Centigrade. Furthermore, these surfaces may be exposed to such temperatures long enough for the sterilization process to be continued. Thus in a preferred embodiment, the housing 16 prevents the CCD 28 from being heated above its degradation temperature despite the housing's exterior reaching greater temperatures during sterilization. Furthermore, though sterilizable versions of the endoscope 12 and coupling optics 32 exist, in a preferred embodiment housing 16 would offer thermal insulation to part or all of these components as well.

The two principal modes by which thermal energy can reach the CCD 28 thereby raising its temperature are conduction and radiation. Calculations show that conduction is by far the predominant mode. Accordingly in a preferred embodiment, the housing 16 is constructed to reduce thermal conduction to the CCD 28. Also in a preferred embodiment, the CCD 28 is mounted within housing 16 so that its thermal connection to the exterior of housing 16 is reduced.

The construction of housing 16 and the positioning of the CCD 28 therein are now further described. In a preferred embodiment, the housing 16 is generally cylindrical with a diameter of about one inch and a length of about three and one-half inches thereby allowing easy manipulation by the operator. Preferably, the housing 16 is constructed of titanium or some other low heat-conducting material. The surface of the housing 16 is comparatively large and as noted above, conduction is the primary mode of heat transfer to the interior of the housing 16 and CCD 28. To reduce the conduction from the housing 16 surface, housing 16 includes double-walled sides comprising outer wall 34a and inner wall 34b which extend for at least a portion of the housing's 16 length, and for at least a portion of the housing's 16 circumference. Between walls 34a, 34b is a vacuum space 36. In a preferred embodiment, inner and outer walls 34a, 34b extend for most of the length of housing 16 and around the entire circumference of housing 16 so there will be only one vacuum space 36.

Inner and outer walls 34a, 34b may comprise two cylinders which include lips 35 on both ends. These two cylinders may be electron beam welded together at lips 35 in substantially concentric alignment. As electron beam welding typically occurs in a vacuum, the vacuum space 36 may be formed as inner and outer walls 34a, 34b are joined. In a preferred embodiment the distance between the inner and outer walls 34a, 34b and thus the dimension of vacuum space 36 is about 0.060 inch.

As noted above, the amount of heat reaching the interior of the housing 16 from radiation is smaller than from conduction. In any event, radiation may be reduced by making the wall surfaces 34c, 34d which are adjacent to the vacuum space 36 and which face each other, reflective. This reduces the emissivity of the walls 34a, 34b and any standard reflective coating or polishing operation may be used.

A cylindrical end bushing 38 may be mounted within the housing 16 in proximity to the housing forward end 20, which serves to couple the endoscope 12 to the housing 16. The endoscope 12 may be coupled to the end bushing through attachment means 39. Preferably, the end bushing 38 is designed to allow rotation of the endoscope 12 relative to the housing 16 so that different areas or orientations of a body cavity may be viewed. The end bushing 38 is also preferably constructed of a plastic such as ULTEM made by General Electric or some other low heat-conducting material which may withstand sterilization temperatures and which minimizes the heat conducted to the inner wall 34b of the housing 16 during sterilization.

To ensure that there is a tight seal between the end bushing 38 and housing 16, an O-ring 40 may extend about the circumference of end bushing 38. A tight seal between the housing 16 and end bushing 38 is also ensured by ring nut 41 which directs end bushing 38 towards stops 42 located on the interior of inner wall 34b. This arrangement provides that the end bushing 38 is securely positioned within housing 16. This tight seal reduces heat transfer into the housing 16 interior as well as prevents contaminants from entering housing 16.

In a preferred embodiment, the end bushing 38 exhibits the electrical insulating properties synonymous with plastic which electrically isolates the housing 16 from the endoscope 12 and patient. This in turn provides that electrical grounding of the housing 16 and backing 24 does not occur through the patient via the endoscope 12.

The backing 24 may be attached to the housing rear end 22 by a press fit or by other suitable means such that it engages the interior of inner wall 34b. An O-ring 44 may extend around the circumference of backing 24 thereby ensuring a tight seal between housing 16 and backing 24. This minimizes thermal flow into the interior of housing 16 and prevents contaminants from entering housing 16 at this junction. The backing 24 is preferably constructed of a low heat-conducting material such as titanium which can withstand sterilization temperatures. As shown in FIG. 1, conduction from the backing 24 to the inner wall 34b is restricted to the annular contact area at the press joint.

In a preferred embodiment, the CCD 28 is mounted on a support member 46 within the housing 16, by use of screws 48. Support member 46 may be attached to the backing 24 by press-fitting it over a circular extension 50 protruding inward from the inside of the backing 24. Support member 46 is preferably cylindrical in shape with varying diameters to accommodate mounting of various components as described herein, and is constructed of a plastic such as ULTEM or some other low heat-conducting material. In a preferred embodiment, the support member 46 is long to increase its thermal path length and thin to minimize its cross-sectional area. This configuration reduces thermal conduction from the backing 24 to the CCD 128 and associated electronics 30 within housing 16. This in turn reduces the rate of any temperature rise of the CCD 28 and electronics 30 during sterilization due to the limited heat which may penetrate into the housing 16.

The support member 46 may support the rear portion 54 of endoscope 12 as well as the coupling optics 32, and may also meet the proximal end 56 of endoscope 12. By supporting these components, the support member 46 ensures optical concentricity by positioning these components in proper alignment with the CCD 28. The long, thin configuration of support member 46 also serves to control the heat flow to the CCD 28 from the end of the endoscope 12.

An infrared filter 58 may also be mounted on the support member 46 so that it is positioned forward of the CCD 28. The filter 58 substantially eliminates the infrared portion of the spectrum of wavelengths directed from the endoscope to the CCD 28 so that the image produced by the CCD 28 results substantially only from visible wavelengths of energy. The filter 58 is sealed against the CCD faceplate 29 by a rubber gasket 59 which excludes dust particles and other contaminants from contacting the CCD faceplate 29. Mounted to the opposite side of the CCD 28 is a heatsink 60 which may be constructed from a material such as aluminum and which may also be mounted on the support member 46. The heatsink 60 serves to increase the thermal mass of the CCD 28 and thereby reduce the rate of temperature rise in the CCD 28 caused by the limited heat which may penetrate into the housing 16. The CCD 28 is also coupled to the electronics 30 which may include a first printed circuit board 62 which itself may also be mounted to support member 46. The screws 48 may be used to mount the CCD 28, heatsink 60 and first printed circuit board 62 all to support member 46.

An electrical connector 64 may be used to couple the first printed circuit board 62 to a second printed circuit board 66 which may also be mounted to support member 46. The individual wires 70 of cable 18 are soldered onto respective locations (not shown) on the second printed circuit board 66 thereby coupling the image from the CCD 28 to the associated camera electronics and video monitor located at the other end of the cable 18.

The circuitry (not shown) of the second printed circuit board 66 may generate heat when transmitting signals as the CCD operates during a surgical procedure. However, this amount of heat is typically small and does not adversely affect the CCD 28 because of the small thermal conductivity of the support member 46 which separates the CCD 28 and second printed circuit board 66. It should be noted that generally the CCD 28 and second printed circuit board 66 do not operate during sterilization. Accordingly, the only heat component of concern during sterilization is that which impinges on the exterior of housing 16.

Cable 18 includes a molded strain relief 78 comprising a high temperature flexible material such as silicone rubber which may withstand sterilization temperatures. Strain relief 78 surrounds a nut 80 that threadably engages interior threads (not shown) of the backing 24. The cable 18 which is typically 0.230 inch in diameter also includes a braided shield 82 that extends from the nut 80 over the entire length of cable 18. The braided shield is the point of entry for heat collected over the entire length of cable 18.

In addition to controlling heat flow to the CCD 28 and other components in housing 16, the housing 16 preferably acts as a shield to suppress electromagnetic interference, and as a gas and water barrier. The tight seals between the housing 16 and end bushing 38 and backing 24 facilitate this blocking capability. Accordingly, in addition to sterilization, the housing 16 may be disinfected by either a cold soak process or by ethylene oxide gas while preventing contaminants from reaching the CCD 28.

Alternatively, the housing 16 may contain more than one CCD 28. For example, the use of two CCDs is desirable to provide the viewer with a stereoscopic three-dimensional image as described in U.S. patent application Ser. No. 07/934,815 filed Aug. 24, 1992 and assigned to Envision Medical Corp., the disclosure of which is incorporated herein by reference as though set forth in full herein. As another example, the use of three CCDs allows the incoming image to be separated into three color components which is desirable where increased light gathering and resolution are required. Similar to the situation where one CCD is used, the use of multiple CCDs requires protection against heat and contaminants.

Figure 2:
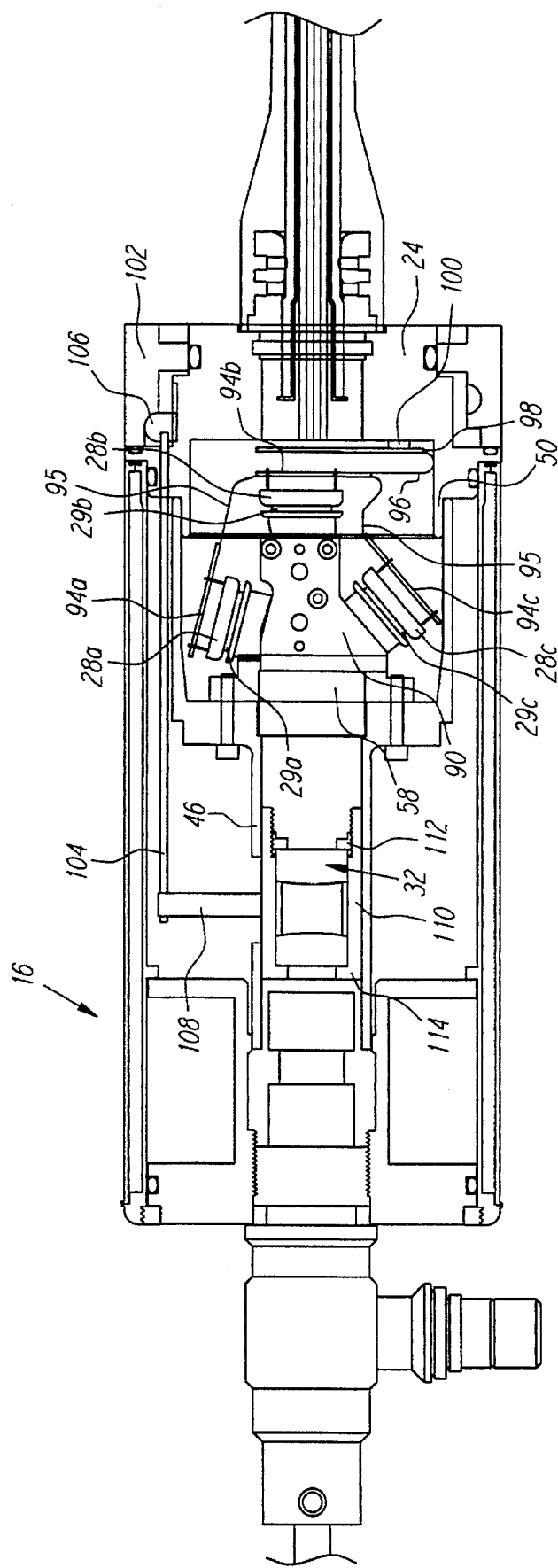
FIG. 2 is a side view of surgical visualization components including a section view of a protective housing containing more than one CCD.

An alternative embodiment is shown in FIG. 2 with like elements similarly numbered as in FIG. 1. As shown, housing 16 contains three CCDs 28a, 28b and 28c. CCDs 28a, 28b and 28c which may provide increased light gathering and resolution capability as noted above, typically require more mounting space than the single CCD 28 described in connection with FIG. 1. Accordingly, the preferred cylindrical support member 46 and housing 16 in this embodiment may be constructed larger to accommodate the use of multiple CCDs. As in FIG. 1, support member 46 may be press-fit onto a circular extension 50 of backing 24. Increasing the volume of housing 16 actually improves thermal protection due to the fact that the volume of a cylinder increases faster than the associated surface area. Thus, the effectiveness of vacuum space 36 increases which may offset any additional heat absorbed by the increased surface of housing 16.

In this embodiment, a prism 90 or some other mirror arrangement (not shown) is positioned between the infrared filter 58 and CCDs 28a, 28b and 28c. As described in connection with FIG. 1, the infrared filter 58 substantially eliminates infrared wavelengths. The prism 90 separates the incoming image into three color components and directs a color component to each of the three CCDs 28a, 28b and 28c through the respective CCD faceplates 29a, 29b and 29c. Similar to a CCD, the coatings and adhesives (not shown) used on the prism 90 degrade with exposure to high temperatures such as those synonymous with sterilization. Accordingly, the thermal protection provided by housing 16 benefits the prism 90 as well.

The three CCDs 28a, 28b and 28c are mounted to the prism via CCD faceplates 29a, 29b and 29c. The CCD faceplates 29 may be attached by a suitable adhesive or clamp directly to the prism 90 which then acts as a large heatsink. As shown in FIG. 2, CCDs 28 need not be mounted to support member 46 but may be contained therein which also provides thermal insulation during sterilization. Three printed circuit board sections 94a, 94b and 94c may be attached to the respective CCDs 28a, 28b and 28c, and are electrically connected by flex sections 95 thereby forming a single rigid-flex circuit board. An additional flex connector section 96 electrically couples the rigid-flex circuit board to a second printed circuit board 98.

The second printed circuit board 98 used in a triple-CCD embodiment typically includes more circuitry and thus generates more heat during operation of the CCDs 28, than the second printed circuit board 66 of the single-CCD embodiment. This in turn may generally create more heat which might impinge on CCDs 28. However as shown in FIG. 2, the primary thermal path between the second printed circuit board 98 and the CCDs 28 comprises the flex connector section 96 and support member 46. Connector section 96 is typically thin and thus a low conductor of heat and as described above, support member 46 is also typically a low heat conductor. Accordingly, the CCDs 28 are at least partially insulated from second printed circuit board 98 by connector section 96 and support member 46.

In any event, a thermal path component 100 may be included to couple the second printed circuit board 98 to the backing 24 thereby directing heat away from the CCDs 28 during operation, and securely positioning second printed circuit board 98. Alternatively, thermal path component 100 may couple the second printed circuit board 98 to the housing 16. Though the second printed circuit board 98 may consequently become hotter during sterilization due to its connection with backing 24 or housing 16, it may be readily constructed to withstand such heat. Once again, the flex connector section 96 and support member 46 would at least partially insulate the CCDs 28 from any heat received by the second printed circuit board 98 during sterilization.

FIG. 2 also shows a user focus adjustment mechanism that could be included with any of the described embodiments (i.e., single or multiple CCD) to improve the useful working distance of the system by varying its focal length. The focus ring 102 which is coupled to backing 24 through adjusting threads or other suitable means, may be rotated by the user (or by electromechanical or other means not shown) about backing 24 thereby moving the push rod 104 by way of the cam ball 106. The push rod extends through a hole in the circular extension 50 of backing 24. The push rod 104 is connected to an arm 108 which extends through a hole in support member 46 so that it engages a lens slider 110. Lens slider 110 securedly houses the coupling optics 32 via ring nut 112 and shoulder 114.

The lens slider 110 may comprise a tube which fits snugly but movably within the preferred cylindrical support member 46. Thus when the push rod 104 and arm 108 move, the lens slider 110 moves within support member 46 thereby moving the coupling optics 32 along the optical axis. This changes the position of the coupling optics 32 with respect to the CCDs 28 thereby varying focal length and increasing the working distance of the system.

As mentioned above, the housing 16 may alternatively contain two CCDs (not shown). As with the triple-CCD embodiment, the housing 16 and support member 46 could be enlarged to accommodate the increased space necessary for mounting the CCDs thereby providing the benefit of increased vacuum space 36. A double-CCD embodiment typically also includes a prism or double mirror to accommodate the two CCDs. However, the double-CCD embodiment generally does not require a printed circuit board which may generate increased heat as described above in connection with the triple-CCD embodiment. Accordingly, a heat path component would typically be unnecessary.

Figure 3:
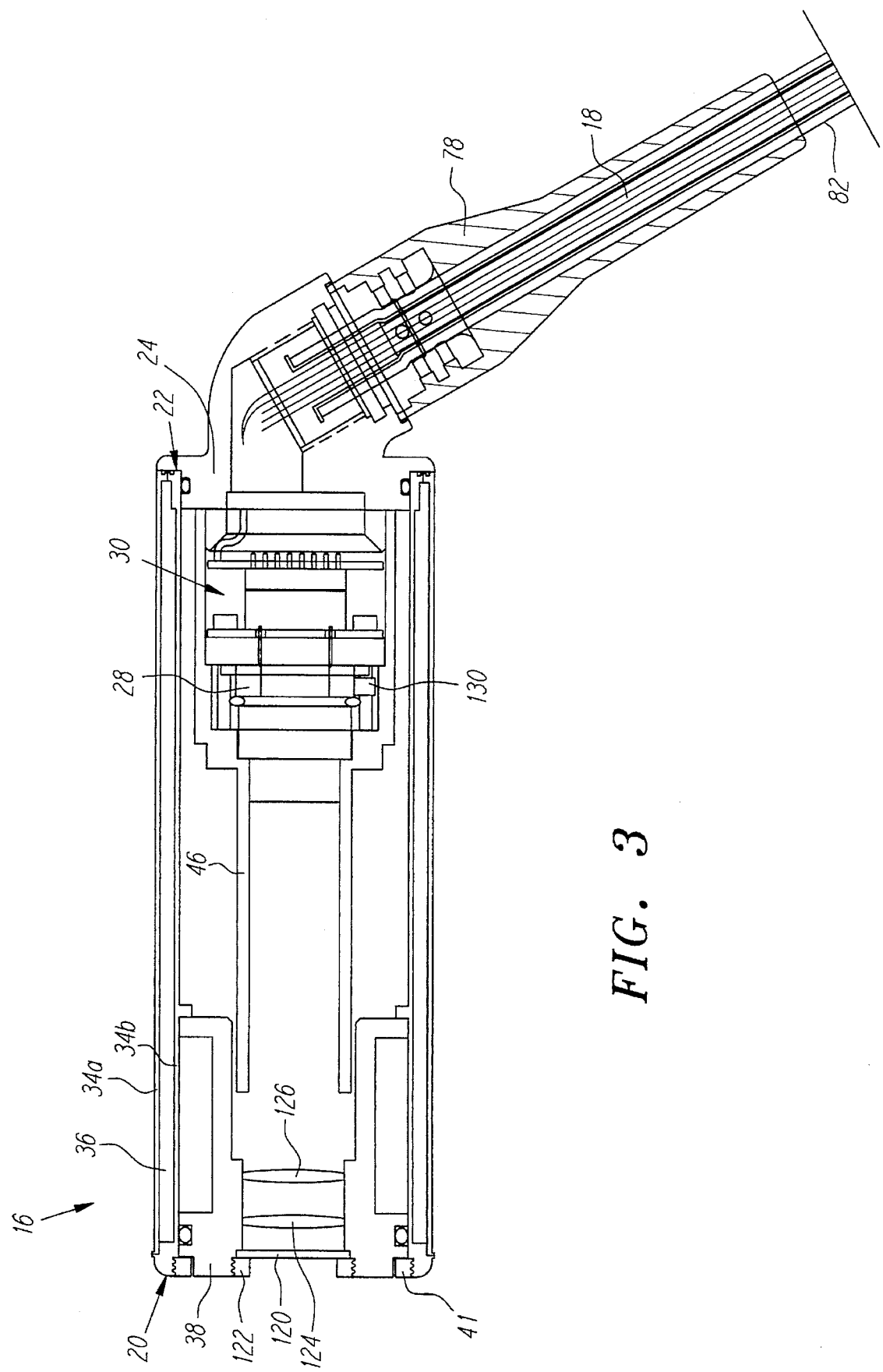
FIG. 3 is a section view of a protective housing containing one CCD.

An alternative embodiment of the current invention for use in observing high-temperature industrial processes is shown in FIG. 3 with like elements similarly numbered as in FIG. 1. In this embodiment, the housing 16 may be placed in a vessel such as a furnace or engine compartment in which the process occurs. Alternatively, the housing 16 may be attached to the exterior of a vessel wall which is equipped with a window or some other observation point. As mentioned earlier, many CCDs exhibit a degradation temperature of about 80 degrees Centigrade. However, because industrial processes such as those within furnaces, engine compartments and/or nuclear generating stations occur above 100 degrees Centigrade, thermal protection for the CCD is necessary.

In this embodiment, a window 120 is mounted to bushing 38 by ring nut 122. Preferably, the window 120 comprises a low-heat conducting material which may withstand high temperatures but which is still optically transparent such as quartz. Alternatively, bushing 38 may be replaced with a cap (not shown) to enclose housing forward end 20 in similar fashion to how the backing 24 encloses the housing rear end 22. Similar to backing 24, the cap preferably comprises a low-heat conducting material such as titanium. The cap may be press-fitted onto housing forward end 20 or secured to the housing 16 by means of a ring nut 41. Again similar to backing 24, the conductive path between the cap and inner wall 34b would be limited to the annular area of contact therebetween. Furthermore, the tight seals between housing 16 and the backing 24 and bushing 38 or cap provide that contaminants associated with the industrial process generally do not enter the housing 16.

Lenses 124, 126 are mounted to the bushing 38, or alternatively to the cap discussed above, so that they are along the optical path between the window 120 and the CCD 28. Lenses 124, 126 direct the image viewed through the window 120 to the CCD 28 at which point the image information is transferred to the electronics 30, and then prepared for transmission to the camera electronics at the distal end of the cable 18.

In this embodiment, the housing may be inserted into the vessel in which the high-temperature process occurs. To secure the housing 16 so that a steady image is received, the housing 16 may be attached to a hole in the vessel wall whereby the exterior of the housing 16 may include threads (not shown) for engagement with corresponding threads located on the edges of the vessel wall hole. Alternatively, the housing 16 may be otherwise attached to an interior wall of the vessel. To the extent that the materials comprising the molded strain relief 78 and braided shield 82 surrounding the cable 18 may be incapable of withstanding the heat present within the vessel, these components should remain outside the vessel.

In any event, the CCD 28 may then be activated to observe the process when the housing 16 is mounted. The vacuum space 36 created by the double walls 34a, 34b provides thermal protection as described above. Because heat might enter housing 16 more readily through the window 120 than the double walls 34a, 34b, CCD 28 is preferably positioned toward the rear of housing 16 as shown in FIG. 3 to increase the thermal path between the window 120 and CCD 28.

The amount of time that the process may be viewed by the CCD 28 depends on the process temperature. Higher process temperatures generally shorten the time that the housing 16 could be exposed to high temperatures before heat sufficient enough to degrade the picture provided by the CCD 28 penetrates the housing 16. To increase exposure time, a heat exchange system 130 coupled to the CCD 28 could be included to direct the heat which eventually arrives at the CCD 28 away therefrom. Typical heat exchange systems include recirculating coolants or thermoelectric coolers such as Peltier devices. A similar heat exchange system or thermal path component (not shown) may also be used to direct any heat produced by the electronics 30 as they operate, away from the CCD 28.

Where the vessel includes an observation point in the vessel wall, housing 16 may be mounted to the exterior of the vessel but in proximity to the observation point so that the window 120 corresponds with the observation point. To this end, housing forward end 20, the bushing 38 or the cap discussed above may include threads or other suitable attachment means which threadably engage or otherwise attach the housing 16 to the vessel wall. Attaching the housing 16 to the exterior of the vessel generally increases exposure time because the heat impinging on the housing 16 is that heat which emanates from the vessel rather than directly from the process as when the housing 16 is mounted inside the vessel.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A sterilizable apparatus for protecting at least one CCD and a portion of an endoscope, comprising:

a housing having a forward end and rear end, the housing including inner and outer walls separated by a vacuum, an exterior of the housing capable of withstanding temperatures of about 130 degrees Centigrade, the housing capable of preventing electromagnetic interference and gaseous and liquid contaminants from reaching an interior of the housing;

an end bushing mounted in the interior of the housing in proximity to the forward end and coupled to the endoscope, the end bushing providing rotation of the endoscope relative to the housing, and comprising a material capable of withstanding temperatures of about 130 degrees Centigrade;

a backing for receiving a cable, the backing comprising a low heat-conducting material and mounted to the housing in proximity to the rear end;

a support member for positioning the at least one CCD within the inner walls so that the at least one CCD is not heated above approximately 80 degrees Centigrade, the support member being made of a low heat-conducting material and having a long, thin configuration for reducing thermal conduction to the at least one CCD, the support member being attached to the backing and extending toward the forward end for engagement with the endoscope;

coupling optics mounted on the support member and coupled to the endoscope and the at least one CCD;

a heatsink coupled to the at least one CCD and mounted to the support member; and electronics mounted on the support member and coupled to the at least one CCD and the cable.

2. An apparatus for protecting at least one CCD from heat external to the apparatus, comprising:

a housing including inner and outer walls containing a vacuum;

a support member comprising a low heat-conducting material mounted within the inner walls of the housing for positioning and thermally insulating the at least one CCD so that the at least one CCD is maintained below its degradation temperature;

a backing mounted to a rear end of the housing;

a coupler mounted in proximity to a forward end of the housing comprising an end bushing mounted to the housing for engaging a surgical visualization device, and for providing rotation of the surgical visualization device relative to the housing, the end bushing comprising a material capable of withstanding temperatures of about 130 degrees Centigrade.

3. The apparatus of claim 2 wherein the surgical visualization device is an endoscope.

4. A method for protecting at least one CCD from external heat, comprising:

providing a housing having inner and outer walls containing a vacuum;

positioning the at least one CCD on a support member, the support member being contained within the inner walls at a location where the at least one CCD is maintained below its degradation temperature, and the support member being made of a low heat-conducting material and having a long, thin configuration for reducing thermal conduction to the at least one CCD;

mounting a backing to a rear end of the housing;

mounting a coupler in proximity to a forward end of the housing, including mounting an end bushing to the housing, the end bushing for engaging a surgical visualization device and for providing rotation of the surgical visualization device relative to the housing, the end bushing comprising a material capable of withstanding temperatures of about 130 degrees Centigrade.

5. The method of claim 4, wherein the surgical visualization device is an endoscope.

* * * * *

UNITED STATES PATENT AND TRADEMARK OFFICE
CERTIFICATE OF CORRECTION

PATENT NO. : 5,587,736
DATED : Dec. 24, 1996
INVENTOR(S) : Robert R. Walls

It is certified that error appears in the above-indentified patent and that said Letters Patent is hereby corrected as shown below:

On the title page, item [73] Assignee: change
"Envision Medical Corporation, Goleta, Calif" to -- Bristol-Myers Squibb Co., New York, N.Y. --
 At column 4, line 61, "128" should be replaced by --28--.

Signed and Sealed this

Twenty-first Day of July, 1998

*Attest:*

BRUCE LEHMAN

*Attesting Officer*          *Commissioner of Patents and Trademarks*